United States Patent
Kandeel

(10) Patent No.: US 11,801,247 B1
(45) Date of Patent: Oct. 31, 2023

(54) METHOD OF TREATING TRYPANOSOMIASIS

(71) Applicant: KING FAISAL UNIVERSITY, Al-Ahsa (SA)

(72) Inventor: Mahmoud Kandeel, Al-Ahsa (SA)

(73) Assignee: KING FAISAL UNIVERSITY, Al-Ahsa (SA)

(*) Notice: Subject to any disclaimer, the term of this patent is extended or adjusted under 35 U.S.C. 154(b) by 0 days.

(21) Appl. No.: 18/132,244

(22) Filed: Apr. 7, 2023

(51) Int. Cl.
*A61K 31/517* (2006.01)
*A61P 33/02* (2006.01)

(52) U.S. Cl.
CPC ............ *A61K 31/517* (2013.01); *A61P 33/02* (2018.01)

(58) Field of Classification Search
CPC .............................. A61K 31/517; A61P 33/02
See application file for complete search history.

(56) References Cited

PUBLICATIONS

Dewar et al., 291(47) J. Bio. Chem. 24768-24778 (2016) (Year: 2016).*
Gibson et al., 10(5) PLOS Neg. Trop. Dis. e0004714 (2016) (Year: 2016).*
Sienkiewicz et al., 69(2) Mol. Microbio. 520-533 (2008) (Year: 2008).*
Kandeel, M. & Suganuma, K., "The Broad-Spectrum Antitrypanosomal Inhibitory Efficiency of the Antimetabolite/Anticancer Drug Raltitrexed," Processes 10(11): 2158 (Oct. 22, 2022).
Dewar, S. et al., "The Role of Folate Transport in Antifolate Drug Action in Trypanosoma brucei," The Journal of Biological Chemistry 291(47): [l/ 24768-24778 (2016).
Richard, D. et al., "A New Type of High Affinity Folic Acid Transporter in the Protozoan Parasite Leishmania and Deletion of Its Gene in Methotrexate-resistance Cells," Membrane Transport Structure Function and Biogenesis 277(33): pp. 29460-29467 (2002).

* cited by examiner

*Primary Examiner* — Timothy R Rozof
(74) *Attorney, Agent, or Firm* — Nath, Goldberg & Meyer; Richard C. Litman

(57) ABSTRACT

Methods of treating trypanosomiasis and, particularly, to methods of treating trypanosomiasis using raltitrexed. Such methods of treatment are useful in, for example, animals selected from the group consisting of cattle, sheep, pigs, goats, horses, and camels.

18 Claims, 2 Drawing Sheets

METHOD OF TREATING TRYPANOSOMIASIS

BACKGROUND

1. Field

The disclosure of the present patent application relates to methods of treating trypanosomiasis and, particularly, to methods of treating trypanosomiasis using raltitrexed.

2. Description of the Related Art

Raltitrexed, a classical antifolate, was the first drug approved for treating advanced colorectal cancer in the United Kingdom in 1996. It is a quinazoline analog with a 6-6 ring-fused structure, like natural folates, and is considered a "classical antifolate". The chemical structure of classical antifolates comprises folate analogs with a pterin ring, an aromatic ring and a glutamate tail. Due to their charged glutamate tail, they are unable to passively diffuse across cell membranes and must be actively transported. Folic acid is required for DNA synthesis in bacteria and other organisms because of its role in the production of nitrogenous bases purine and pyrimidine. As the prevalence of infectious diseases rises, there is an urgent need for the discovery of new therapies.

Trypanosomiasis is a devastating and fatal blood protozoal disease affecting humans and animals worldwide. The *Trypanosoma cruzi* parasite that causes Chagas disease is already present in 21 countries across Latin America and the southern United States. More than 7 million individuals are infected with Chagas disease at present, causing 10,000 deaths annually from its complications, and another 70 million are at risk of infection. Human African trypanosomiasis (HAT), often known as sleeping sickness, remains one of Africa's most dreaded and lethal diseases, affecting an estimated 70 million people across 36 nations in sub-Saharan Africa.

The safety and toxicity of many anti-trypanosomal medicines are extremely poor. New kinds of anti-trypanosomal drugs that are more effective and have lower host toxicity need to be discovered. There is an immediate need for effective, safe and cost-effective anti-trypanosomal medications because of microbial resistance to the few traditional anti-trypanosomal drugs, increasing vector resistance to insecticides, a lack of effective vaccinations and the side effects of the present drugs.

Because conventional antifolates are strongly negatively charged chemicals that cannot enter the bacterial cell membrane, their utility as antimicrobials have been limited. As a result, almost all commercially available antibacterial folates fall into the non-classical group of antifolates.

Thus, a method of treating trypanosomiasis solving the aforementioned problems is desired.

SUMMARY

The present subject matter is directed to a method of treating trypanosomiasis in a subject comprising administering a therapeutically effective amount of raltitrexed to a subject in need thereof. In an embodiment, the trypanosomiasis is caused by one or more trypanosome species selected from the group consisting of *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000. In an embodiment, the trypanosome species can cause a disease in at least one of blood and tissues of the subject. In an embodiment, the trypanosome species can cause a disease in tissues of the subject. In an embodiment, the subject is an animal selected from the group consisting of cattle, sheep, pigs, goats, horses, and camels.

In one embodiment, the present subject matter relates to a method of treating trypanosomiasis in a subject caused by a trypanosome species causing a disease in tissues. In an embodiment, the subject is an animal selected from the group consisting of cattle, sheep, pigs, goats, horses, and camels.

In a further embodiment, the present subject matter relates to a method of treating an animal for trypanosomiasis, the animal being selected from the group consisting of cattle, sheep, pigs, goats, horses, and camels. In an embodiment, the trypanosomiasis is caused by a tissue trypanosome, a trypanosome species, or a trypanosome affecting tissues of the animal. In an embodiment, the animal is selected from horses and camels. In an embodiment, the animal is a horse and the trypanosome species is *T. equiperdum*. In an embodiment, the animal is a camel and the trypanosome species is *T. evansi*. In an embodiment, the species is *T. congolense*.

These and other features of the present subject matter will become readily apparent upon further review of the following specification.

DETAILED DESCRIPTION OF THE PREFERRED EMBODIMENTS

Figure 1A:
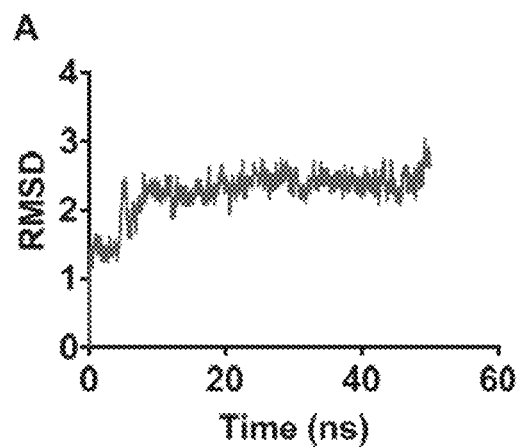
FIGS. 1A-1B are graphs (A) RMSD calculation of the raltitrexed-*Trypanosoma brucei* dihydrofolate reductase complex for 50 ns.; (B) RMSF calculation of the raltitrexed-*Trypanosoma brucei* dihydrofolate reductase complex for 50 ns.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a 10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter is directed to a method of treating trypanosomiasis in a subject comprising administering a therapeutically effective amount of raltitrexed to a subject in need thereof. Raltitrexed can target the major enzymes required for folic acid metabolism, which is required to maintain microbial species integrity. For example, as raltitrexed is a thymidylate synthase (TS) inhibitor, it can act as an antibacterial agent because DHFR-TS catalyzes the reduction of folate or 7,8-dihydrofolate to tetrahydrofolate and intimately couples with DHFR-TS. Targeting DHFR-TS eventually inhibits the catalysis of folic acid to its constituents which ultimately stops the synthesis of DNA, and the integrity of microbial cells can be disturbed.

As described herein, raltitrexed is an effective anti-trypanosomal agent against at least six different trypanosome species, including *T. b. brucei* (TbbGUTat 3.1) *T. b. rhodesiense* (TbrIL1501), *T. b. gambiense* (TbgIL1922), *T. evansi* (Tev Tansui), *T. equiperdum* (Teq IVM-t1), and *T. congolense* (Tc) IL3000. As described herein, in silico studies demonstrated robust binding of raltitrexed with TbDHFR-TS.

In an embodiment, a method of treating trypanosomiasis in a subject, comprises administering a therapeutically effective amount of raltitrexed to a subject in need thereof. In a particular embodiment, the trypanosomiasis is caused by one or more trypanosome species selected from the group consisting of *T. b. brucei* (TbbGUTat 3.1), *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000.

In an embodiment, the trypanosome species can cause a disease in at least one of blood and tissues of the subject. In an embodiment, the trypanosome species can cause a disease in tissues of the subject. In an embodiment, the subject is an animal selected from the group consisting of cattle, sheep, pigs, goats, horses, and camels. In an embodiment, the subject is a horse and the trypanosome species is *T. equiperdum*. In an embodiment, the trypanosome species causes equine genital trypanosomiasis. In an embodiment, the subject is a camel and the trypanosome species is *T. evansi*. In an embodiment, the species is *T. congolense*.

As described herein, raltitrexed demonstrated broad-spectrum trypanocidal activity against *Trypanosoma* in MD simulations and using in silico analysis. The estimated IC50 was determined to be in the range of 8.88-22.53 g/ml, showing low micromolar inhibition of *Trypanosoma*.

In one embodiment, the present subject matter relates to a method of treating trypanosomiasis caused by a trypanosome species causing a disease in tissues of the subject. In an embodiment, the trypanosome species is selected from the group consisting of *T. evansi* (Tev) Tansui and *T. equiperdum* (Teq). In an embodiment, the subject is an animal selected from the group consisting of cattle, sheep, pigs, goats, horses, and camels. In an embodiment, the animal is selected from the group consisting of horses and camels. In an embodiment, the subject is a horse and the trypanosome species is *T. equiperdum*. In an embodiment, the trypanosome species causes equine genital trypanosomiasis. In an embodiment, the subject is a camel and the trypanosome species is *T. evansi*. In an embodiment, the trypanosome species is *T. congolense*.

In a further embodiment, the present subject matter relates to a method of treating an animal for trypanosomiasis, the animal being selected from the group consisting of cattle, sheep, pigs, goats, horses, and camels. In an embodiment, the trypanosomiasis is caused by a tissue trypanosome or a trypanosome affecting tissues of the animal. In an embodiment, the animal is selected from the group consisting of horses and camels. In an embodiment, the animal is a horse and the trypanosome species is *T. equiperdum*. In an embodiment, the animal is a camel and the trypanosome species is *T. evansi*. In an embodiment, the trypanosome species is *T. congolense*.

Traditionally, trypanocidal drugs that have been effective for inhibiting a particular species of trypanosomes, have not been effective for inhibiting other species of trypanosomes. This is generally attributed to morphological and structural distinctions between the species and holds especially true for trypansomes affecting horses and camels. *T. Equiperdum* is a species of kinetoplastid parasites that causes Dourine disease or covering sickness in horses and other animals in the family equidae. *T. equiperdum* is the only trypanosome that is not spread by an insect vector and can be transmitted through the venereal route. *T. evansi* is the broadest spectrum member of trypanosomes that infects a wide range of animal hosts. It has morphological and structural distinctions from other known trypanosomes and the discovery of specific drugs specific for this species is recommended.

Dourine disease is known for being highly resistant to treatment (Cauchard, J., D. Carnicer, A. Madeline, E. Guitton, A. Giraudet, P. Büscher, L. Hebert, and C. Laugier. "Evaluation of Melarsamine hydrochloride (Cymelarsan®) efficacy for the treatment of dourine nervous form on experimentally infected ponies." *J Equine Vet Sci* 39 (2016): S51.). Many trypanocidal drugs that have been used in the treatment of Dourine have shown variable results, with chronic cases being particularly unresponsive to treatment. To get effective results, repeated administration or combination of more than one drug has been required. Given that, most of the currently available anti-trypanosomal drugs have narrow safety margin (https://www.sciencedirect.com/book/9780702052460/veterinary-medicine, Diseases Primarily Affecting the Reproductive System). The four main drugs on the market that are used to treat the clinical signs of Dourine, namely Suramin, Diminazen, Cymelarsan, and Quinapyramin, do not provide a cure and animals treated with these drugs typically experience relapses.

Raltitrexed can be administered at a therapeutically or pharmaceutically effective dosage, e.g., a dosage sufficient to provide treatment for trypanosomiasis. Administration of raltitrexed or pharmaceutical compositions thereof can be by any method that delivers raltitrexed systemically and/or locally. These methods include oral routes, parenteral routes, intraduodenal routes, and the like.

While dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing raltitrexed for treatment of trypanosomiasis, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The raltitrexed can also be administered in sustained or controlled release dosage forms, including depot injections, osmotic pumps, pills, transdermal (including electrotransport) patches, and the like, for the prolonged administration at a predetermined rate, preferably in unit dosage forms suitable for single administration of precise dosages.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the raltitrexed, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. raltitrexed and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. Percentages of raltitrexed of 0.01% to 10% in solution are employable and may be higher if the composition is a solid which will be subsequently diluted to the above percentages. The composition may comprise 0.2% to 2% of theraltitrexed in solution.

Nasal solutions of the raltitrexed alone or in combination with other pharmaceutically acceptable excipients can also be administered.

Formulations of the raltitrexed or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present teachings are illustrated by the following examples.

EXAMPLES

Materials

Raltitrexed was purchased from ApexBio (Houston, TX, USA), and CultureSure DMSO was obtained from Wako Pure Chemical (Osaka, Japan). T. b. *brucei* (Tbb) GuTat3.1, T. b. rhodesiense (Tbr) IL1501, T. b. gambiense (Tbg) IL1922 (isolated from Ivory Coast), *T. evansi* (Tev) Tansui (isolated from Taiwan), *T. equiperdum* (Teq) IVM-t1 and *T. congolense* (Tc) IL3000 were also obtained for this study. A 96-well Optical bottom plate was purchased from ThermoFisher SCIENTIFIC (Waltham, MA, USA). CellTiter-Glo Luminescent cell viability reagent and GloMax plate reader were purchased from Promega Corporation (Fitchburg, WI, USA). Hiram's modified Isocove's Dulbecco's medium (HMI-9), HEPES, pyruvic acid sodium salt, BSA, thymidine, 2-mercaptoethanol, L-cysteine, bathocuproine and hypoxanthine were purchased from Sigma-Aldrich (Tokyo, Japan). A basic plate shaker was obtained from IKA® JAPAN (K.K., Osaka, Japan).

Example 1

Anti-Trypanosomal Assay

The trypanocidal activity of raltitrexed was evaluated. The trypanosomes were cultured at 37° C. for Tbb, Tbg, Tbr, Teq and Tev and 33° C. for Tc in an incubator at 5% $CO_2$ using HMI-9 supplemented with 20% heat-inactivated fetal calf serum, 60 mM HEPES, 10 µg/L insulin, 0.1 mM bathocuproine, 5.5 µg/L transferrin, 1 mM pyruvic acid sodium salt, 1 mM hypoxanthine, 16 µM thymidine, 6.7 ng/L sodium selenite, 0.0001% 2-$-mercaptoethanol, 2 mM L-cysteine and 0.4 g/L BSA. Trypanosomes were subcultured every two days. Raltitrexed was dissolved in DMSO: $H_2O$ (1:10, v/v). The effect of the solvent was assessed to be negligible on the parasite.

Initially, raltitrexed was examined at two concentrations of 25 and 0.25 µg/ml to check the possible extended spectrum opportunities against six trypanosomes. The initial screening revealed that raltitrexed showed promising trypanocidal activities at 25 µg/mL. As a confirmed inhibitor, the IC50 of raltitrexed was evaluated using serial dilution from 25 µg/mL to 0.78 µg/mL. This range was effective in the accurate estimation of the IC50 of the compound. After three days of cultivation, 25 µL of CellTiter-Glo Luminescent cell viability reagent were aliquoted into each well, and the plate was shaken for 500 shakes/min by an MS3 basic plate shaker for 30 s to facilitate cell lysis and release intracellular ATP. After mixing, the bioluminescence of each well was measured using a Glomax plate reader.

Example 2

Docking Studies

Docking studies were performed to determine the binding potential of raltitrexed (shown below) with TbDHFR-TS. The protein, ligand and docking processes were carried out as previously described, with minor alterations. In all docking steps, the Schrodinger Maestro suit (Schrodinger LLC, New York, NY, USA) was employed.

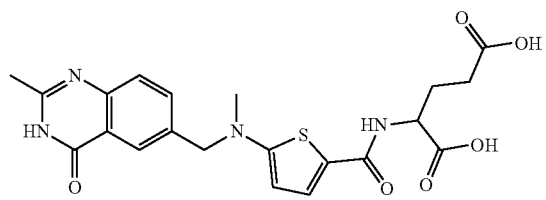 [SMILES: Cc1nc2ccc(CN(C)c3ccc(C(=O)NC(CCC(=O)O)C(=O)O)s3)cc2c(=O)[nH]1]

Raltitrexed

Example 3

Macromolecule and Compounds Retrieval and Preparation

The compounds' 2D structures were obtained from the PubChem website, loaded using Ligprep, and then 3D optimized at optimal physiological pH. The Protein Data Bank was used to retrieve the protein structure file (PDB, 3RG9), which constitutes a TbDHFR structure in complex with WR99210 at 2.00 Å resolution.

Using the protein preparation module, the macromolecule structure was optimized for docking. Crystallographic chemicals and water molecules were removed from the solution. The protein was protonated by adding polar hydrogens, and the structures were optimized and the energy was reduced using the OPLS2005 force field. WR99210 was used as the center of a 20 Å grid box for docking grid generation.

Example 4

Docking Runs

The standard precision SP Glide docking methodology was utilized. Scores were used to rank the output results. Redocking of WR99210 was used to assess the correctness of the docking run, and the docking pose demonstrated complete complementarity and low RMSD when compared to the bound ligand.

Example 5

Molecular Dynamics Simulation

A molecular dynamics simulation lasting 50 ns was performed using Desmond software according to the previously performed protocol. Docking studies provided the protein-ligand complexes needed for molecular dynamics simulation. In static conditions, binding status of a ligand can be predicted by molecular docking studies. Predictions of ligand binding in a physiological setting were simulated. The Protein PreparationWizard or Maestro was used to perform complex optimization and minimization prior to actual protein-ligand complex preparation. The System Builder application was used to set up all the systems. Tip3P opted for the Solvent Model, which features a square orthorhombic box (Transferable Intermolecular Interaction Potential 3 Points). The simulation makes use of the OPLS 2005 force field. When necessary, counter ions were added to the models to achieve electrical neutrality. Physiological conditions were mimicked by adding 0.15 M NaCl. As the simulation was conducted at a constant 300 K and 1 atm, the NPT ensemble of the OPLS 2005 force field. When necessary, counter ions were added to the models to achieve electrical neutrality. Physiological conditions were mimicked by adding 0.15 M NaCl. As the simulation was conducted at a constant 300 K and 1 atm, the NPT ensemble was used (Isothermal-Isobaric: moles (N), pressure (P) and temperature (T) are all conserved).

Before running the simulation, the models were softened. Trajectories were saved at 100 ps intervals so that the RMSD of the protein and ligand could be calculated over time and used to assess the stability of the simulations.

MS Excel and GraphPad Prism were used to handle and present all the data. The data were reported as Mean SD or, in some cases, as the mean plus range. Changes in each isolation parameter were expressed using descriptive statistics.

Example 6

Trypanocidal Assay

Initially, raltitrexed was examined at 0.25 or 25 μg/mL, constituting high and low concentrations of the drug (Table 1). Raltitrexed showed broad-spectrum trypanocidal actions. At 25 μg/mL, raltitrexed suppressed all the test strains. Stronger action was noticed on TbbGUTat3.1, TbrIL1501, TbgIL1922, Tev Tansui and Teq IVM-t1 by showing more than 99% inhibition rate (Table 1). However, a low trypanocidal rate was observed for TcIL3000.

TABLE 1

The inhibition rate of ralfitrexed at 0.25 or 25 μg/mL against 6 *Trypanosoma* species, TeIL3000, TbbGUTat3.1, TbrIL1501, TbgIL1922, Tev Tansui and Teq IVM-t1.

| | Raltitrexed | |
|---|---|---|
| Trypanosome | Inhibition Rate at 25 μg/mL * | Inhibition Rate at 0.25 μg/mL * |
| TcIL 3000 | 1.77 ± 2.5 | 0 |
| TbbGUTat3.1 | 99.47 ± 0.07 | 0 |
| TbrIL1501 | 99.68 ± 0.16 | 1.01 ± 1.4 |
| TbgIL1922 | 99.6 ± 0.33 | 0 |
| Teq Tansui | 99.9 ± 0.12 | 0 |
| Teq IVM-t1 | 99.8 ± 0.027 | 0 |

* The values are represented as (mean ± SD).

In light of raltitrexed's potential in vitro anti-trypanosomal activity, the IC50 was determined in the presence of various doses of the molecule. The IC50 for raltitrexed was found to be in the range of 5.18-24.13 μg/mL, indicating that it possessed potent anti-trypanosomal activity (Table 2). The strongest trypanocidal activity was found in Teq IVM-t1 with IC50=5.18_0.53 g/mL, while TcIL3000 showed the highest resistance to the trypanosomal activity of raltitrexed with IC50>25 μg/mL. The strength of the trypanocidal actions of raltitrexed was in the following order Teq IVM-t1>Tev Tansui>TbrIL1501>TbgIL1922>TbbGUTat3.1>TcIL3000.
Table 2 shows the IC50 of raltitrexed against six *Trypanosoma* species, TcIL3000, TbbGUTat3.1, TbrIL1501.

TABLE 2

| | Raltitrexed | |
|---|---|---|
| Trypanosome | Inhibition Rate at 25 μg/mL * | Inhibition Rate at 0.25 μg/mL * |
| TcIL3000 | 1.77 ± 2.5 | 0 |
| TbbGUTat3.1 | 99.47 ± 0.07 | 0 |
| TbrIL1501 | 99.68 ± 0.16 | 1.01 ± 1.4 |
| TbgIL1922 | 99.6 ± 0.33 | 0 |
| Tev Tansui | 99.9 ± 0.12 | 0 |
| Teq IVM-t1 | 99.8 ± 0.027 | 0 |

* The values are represented as (mean = SD).

Nanomolar potency against *T. brucei* was determined for methotrexate, pemetrexed and raltitrexed in thymidine and folate-deficient medium. Adding folate and thymidine decreased the effectiveness of the antifolates, with the exception of nolatrexed. The addition of thymidine decreased the effectiveness of raltitrexed more so than the addition of folate.

Figure 2A:
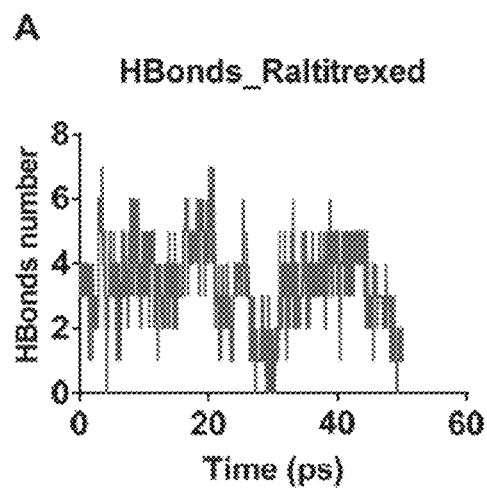
FIGS. 2A-2B are graphs showing (A) radius of gyration (ROG) during interaction of raltitrexed with *T. brucei* dihydrofolate reductase (B) number of hydrogen bonds that were formed during a 50 ns simulation between raltitrexed and *T. brucei* dihydrofolate reductase.

Given the interactions and inhibition of DHFR-TS with raltitrexed, it was modeled with TbDHFR-TS to verify its binding conformations and binding potency. Raltitrexed had a docking score of −7.78, compared to −4.6 for the co-crystalized ligand WR99210 (Table 3), indicating the possibility of significant strong interaction with TbDHFR-TS. The binding of raltitrexed was supported by both favorable hydrogen bonds and lipophilic interaction scores. Because of its superior ligand efficiency, lower hydrogen bond score and lower Lipo score (Table 3), raltitrexed formed more robust contact than WR99210 (FIGS. 2A,B). of thymidine decreased the effectiveness of raltitrexed more so than the addition of folate. The medium used to incubate the trypanosomes in the study contained 1 mg/L folic acid and thymidine at a final concentration of 16 μM. Even though these two substances, folic acid and thymidine, were present in the culture media, inhibitory qualities were visible. This may further support the hypothesis that raltitrexed effects include mechanisms other than folate synthesis. This observation might be species-specific and varies according to the nature of DHFR-TS mutation or amino acid changes.

TABLE 3

The docking score and binding parameters for raltitrexed and the compound WR99210 with *T. brucei* dihydrofolate reductase.

| Title | Docking Score | Glide Ligand Efficiency | Glide Hbond | Glide Lipo |
|---|---|---|---|---|
| Raltitrexed | −7.78 | −0.24 | −0.3 | −3.1 |
| WR99210 | −4.6 | −0.19 | −0.1 | −1.7 |

Inspection of the mode of binding of raltitrexed with TbDHFR-TS indicated a favorable binding mode supported by hydrogen bonding with the side chain of ILE17 and with LY44 and stacking interaction PHE94, which helps in orientation and fixation into the active site of TbDHFR-TS.

Raltitrexed was found to be an inhibitor for the DHFR and TS activities of TbDHFR-TS with IC50 values of 93.1 and 215 nM, respectively. Trimethoprim, pyrimethamine and raltitrexed were reported to function as powerful competitive inhibitors of *T. brucei* DHFR with Ki values of 11.4_1.2, 17.6_2.3 and 70.4_7.2 nM, respectively. To gain a better understanding of how raltitrexed interacts with humans and *T. brucei* DHFR, comparative docking, protein sequence alignment and alignment satisfaction were all compared. The docking score, as well as the ligand efficiency, was a little bit higher with TbDHFR (Table 4). The carboxylate group of raltitrexed was more interactive with human DHFR. Hydrogen bonds and a salt bridge were formed between raltitrexed and the side chains of GLU30, ASN64 and ARG70. The pairwise alignment showed approximately 34 gaps and 175 amino acid differences between the human and *T. brucei* enzymes. These distinctions accounted for approximately 28.31% of the identity percentage. A low homology rate and a significant number of differences could serve as a foundation for designing more selective anti-trypanosomal medicines. Further, raltitrexed chemical modifications targeting the terminal charged atoms are likely to reduce the affinity for human DHFR without reducing the affinity for the parasitic enzyme.

TABLE 4

The docking score and binding parameters for raltitrexed with human (PDB ID IDRF) or *T. brucei* DHFR.

| Title | Docking Score | Glide Ligand Efficiency | Glide Hbond | Glide Lipo |
|---|---|---|---|---|
| *T. brucei* | −7.78 | −0.24 | −0.3 | −3.1 |
| Human | −7.2 | −0.22 | −0.32 | −2.9 |

Figure 1B:
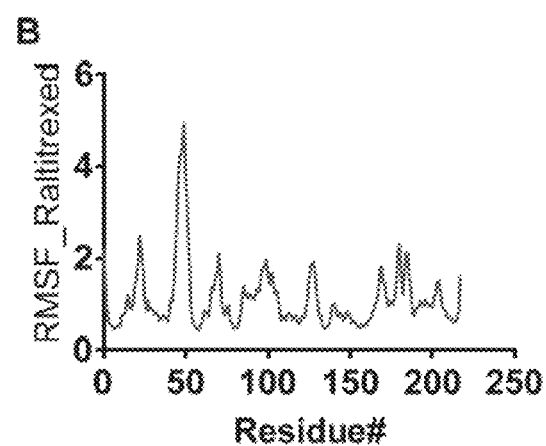
Figure 2B:
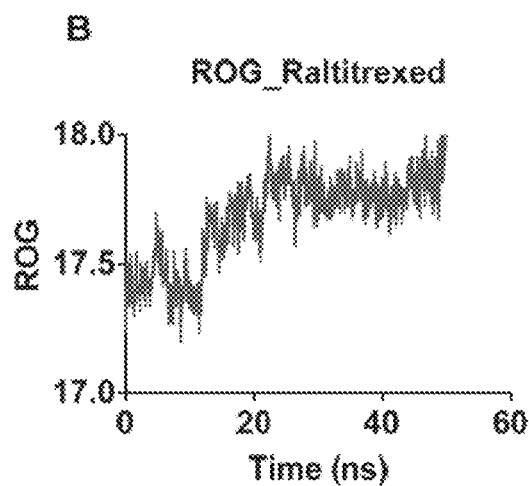

RMSD was calculated for the raltitrexed-TbDHFR-TS complex. The RMSD graph (FIGS. 1A-1B) show that the structure remained stable throughout time with some fluctuation within the range of ~1 Å, which is a normal aspect of the globular protein. The raltitrexed-TbDHFR-TS complex reached five ns at the start of the simulation. These findings support the observed scores and the strong binding of raltitrexed with TbDHFR-TS. The raltitrexed-TbDHFR-TS complex showed low RMSF and indicated modest variations of amino acid residues, with the exception of a flexible loop made up of residue no. 45-55(FIG. 1B). The total number of hydrogen bonds formed between raltitrexed and TbDHFR-TS was traced during 50 ns simulation. The hydrogen bonding statistics indicated that hydrogen bonds ranged from 0-7 with a mean value of 3.38 f 1.3. This indicates the fixation and consistent binding of raltitrexed with TbDHFR-TS. The slight changes (FIG. 2A-2B) in ROG indicate the general compactness of the raltitrexed-TbDHFR-TS complex.

Coadministration of DHFR (dihydrofolate reductase) and DHPS (dihydropteroate synthase) inhibitors are the most widely used antifolate-based antibacterial treatment as it has a broad spectrum of action by killing both Gram-negative and Gram-positive types of bacteria effective against drug-resistant bacteria (*Stenotrophomonas maltophilia*, methicillin-resistant *Staphylococcus aureus*) with minimum side effects.

Raltitrexed affects a wide range of trypanosomes. This range has highly distinct host characteristics; in addition to *T. brucei* species, *T. evansi* affects camels, cattle, horses and dogs. Furthermore, *T. equierdum* is a parasite that infects horses and other equines. The examined trypanosomes impact a wide range of tissue infections. In addition to the well-known blood protozoal illness caused by trypanosomes, *T. equiperdum* is well-known for its genital tract infection and for being a venereal disease that is not spread by an insect vector. The variety of species included in the studies described herein, as well as their host range and diverse diseased tissues, indicated that raltitrexed could be used to treat diseases such as dourine in equines and in camels and other animals.

It is to be understood that the method of treating trypanosomiasis is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating trypanosomiasis in a subject, comprising:
   administering a therapeutically effective amount of raltitrexed to a subject in need thereof, wherein
   the trypanosomiasis is caused by a trypanosome species selected from the group consisting of one or more of *T. evansi* (Tev) Tansui, *T. equiperdum* (Teq) IVM-t1 and *T. congolense* (Tc) IL3000.

2. The method of claim 1, wherein the trypanosome species causes a disease in at least one of blood and tissues of the subject.

3. The method of claim 1, wherein the subject is an animal selected from the group consisting of cattle, sheep, pigs, goats, horses, and camels.

4. The method of claim 1, the subject is a horse and the trypanosome species is *T. equiperdum*.

5. The method of claim 1, wherein the subject is a camel and the trypanosome species is *T. evansi*.

6. The method of claim 1, wherein the species is *T. congolense*.

7. A method of treating trypanosomiasis in a subject, comprising:
   administering a therapeutically effective amount of raltitrexed to a subject in need thereof, wherein the trypanosomiasis is caused by a trypanosome species causing a disease in tissues of the subject, and wherein the trypanosome species is selected from the group consisting of *T. evansi* (Tev) Tansui, *T. congolense*, and *T. equiperdum* (Teq).

8. The method of claim 7, wherein the subject is an animal selected from the group consisting of cattle, sheep, pigs, goats, horses, and camels.

9. The method of claim 7, wherein the trypanosome species causes equine genital trypanosomiasis.

10. The method of claim 7, wherein the subject is a horse and the trypanosome species is *T. equiperdum.*

11. The method of claim 7, wherein the subject is a camel and the trypanosome species is *T. evansi.*

12. The method of claim 7, wherein the trypanosome species is *T. congolense.*

13. A method of treating trypanosomiasis in an animal, comprising:

administering a therapeutically effective amount of raltitrexed to an animal in need thereof, wherein the animal is selected from the group consisting of cattle, sheep, pigs, goats, horses, and camels, and wherein the trypanosomiasis is caused by a trypanosome species selected from the group consisting of *T. evansi* (Tev) Tansui, *T. congolense*, and *T. equiperdum* (Teq).

14. The method of claim 13, wherein the trypanosomiasis is caused by a tissue trypanosome.

15. The method of claim 13, wherein the animal is selected from the group consisting of horses and camels.

16. The method of claim 13, wherein the animal is a horse and the trypanosome species is *T. equiperdum.*

17. The method of claim 13, wherein the animal is a camel and the trypanosome species is *T. evansi.*

18. The method of claim 13, wherein the trypanosome species *T. congolense.*

* * * * *